(12) United States Patent
Hoekstra et al.

(10) Patent No.: US 11,051,514 B2
(45) Date of Patent: Jul. 6, 2021

(54) ANTIFUNGAL COMPOUNDS

(71) Applicant: Mycovia Pharmaceuticals, Inc., Durham, NC (US)

(72) Inventors: William J. Hoekstra, Durham, NC (US); Christopher M. Yates, Raleigh, NC (US); Robert J. Schotzinger, Raleigh, NC (US); Michael R. Loso, Carmel, IN (US); Gary D. Gustafson, Zionsville, IN (US); Michael T. Sullenberger, Westfield, IN (US); Kimberly Steward, Indianapolis, IN (US); Javier Delgado, Indianapolis, IN (US); Xuelin Wang, Carmel, IN (US)

(73) Assignee: Mycovia Pharmaceuticals, Inc., Durham, NC (US)

( * ) Notice: Subject to any disclaimer, the term of this patent is extended or adjusted under 35 U.S.C. 154(b) by 37 days.

(21) Appl. No.: 15/574,775

(22) PCT Filed: May 17, 2016

(86) PCT No.: PCT/US2016/032877
§ 371 (c)(1),
(2) Date: Nov. 16, 2017

(87) PCT Pub. No.: WO2016/187201
PCT Pub. Date: Nov. 24, 2016

(65) Prior Publication Data
US 2019/0216087 A1 Jul. 18, 2019

Related U.S. Application Data

(60) Provisional application No. 62/163,106, filed on May 18, 2015.

(51) Int. Cl.
*A01N 43/653* (2006.01)
*C07D 401/06* (2006.01)

(52) U.S. Cl.
CPC ......... *A01N 43/653* (2013.01); *C07D 401/06* (2013.01)

(58) Field of Classification Search
CPC .......................... A01N 43/653; C07D 401/06
See application file for complete search history.

(56) References Cited

U.S. PATENT DOCUMENTS

| | | | |
|---|---|---|---|
| 4,690,942 A | 9/1987 | Frick et al. | |
| 5,364,938 A | 11/1994 | Dickinson et al. | |
| 8,748,461 B2 | 6/2014 | Hoekstra et al. | |
| 8,796,001 B2 | 8/2014 | Hoekstra et al. | |
| 9,220,265 B2 | 12/2015 | Hoekstra et al. | |
| 8,796,001 C1 | 3/2017 | Hoekstra et al. | |
| 2009/0239748 A1 | 9/2009 | Dietz et al. | |
| 2011/0015158 A1 | 1/2011 | Schotzinger et al. | |
| 2013/0005729 A1 | 1/2013 | Hoekstra et al. | |
| 2013/0005752 A1 | 1/2013 | Hoekstra et al. | |

FOREIGN PATENT DOCUMENTS

| | | |
|---|---|---|
| CN | 103764647 B | 5/2016 |
| ES | 2151223 T3 | 12/2000 |
| JP | S59163374 A | 9/1984 |
| JP | H02-104583 A | 4/1990 |
| JP | H07-502022 A | 3/1995 |
| JP | 2001-519417 A | 10/2001 |
| JP | 2010-510248 A | 4/2010 |
| JP | 2012-529472 A | 11/2012 |
| JP | 2014-516092 A | 7/2014 |
| JP | 2014-517068 A | 7/2014 |
| JP | 2014-517090 A | 7/2014 |
| JP | 2014-518220 A | 7/2014 |
| KR | 1020147001300 A | 4/2014 |
| WO | WO 89/05801 A1 | 6/1989 |
| WO | WO 93/07139 A1 | 4/1993 |
| WO | WO 2008/064311 A2 | 5/2008 |
| WO | WO 2008/124131 A1 | 10/2008 |
| WO | WO 2009/020323 A2 | 2/2009 |
| WO | WO 2010/146113 A1 | 12/2010 |
| WO | WO 2010/147302 A2 | 12/2010 |
| WO | WO 2011/133875 A2 | 10/2011 |
| WO | WO 2011/134911 A2 | 11/2011 |
| WO | WO 2012/177608 A1 | 12/2012 |
| WO | WO 2012/177635 A1 | 12/2012 |
| WO | WO 2012/177728 A1 | 12/2012 |
| WO | WO 2013-047308 A1 | 4/2013 |
| WO | WO 2014/193974 A1 | 12/2014 |

OTHER PUBLICATIONS

Saji, Ikutaro, et al. "Stereoselective Synthesis of Antifungal Agent threo-2-(2,4-Difluorophenyl)-3-methylsulfonyl-1-(1 H-1,2,4-triazol-1-yl)-2-butanol (SM-8668)." Bulletin of the Chemical Society of Japan 67.5 (1994): 1427-1433.*

Alfonsi, Kim, et al. "Green chemistry tools to influence a medicinal chemistry and research chemistry based organisation." Green Chemistry 10.1 (2008): 31-36.*

Extended European Search Report dated Oct. 24, 2014 in connection with EP 12803318.0

Extended European Search Report dated Jun. 20, 2016 in connection with EP 16164223.6.

(Continued)

*Primary Examiner* — John Pak
*Assistant Examiner* — Daniel L Branson
(74) *Attorney, Agent, or Firm* — Wolf, Greenfield & Sacks, P.C.

(57) ABSTRACT

The present invention relates to compounds of Formula (I): wherein $R_1$ is as defined herein, or an acceptable salt, solvate, prodrug or hydrate thereof. The compounds of Formula I are inhibitors of metalloenzymes, such as lanosterol demethylase (CYP51).

(I)

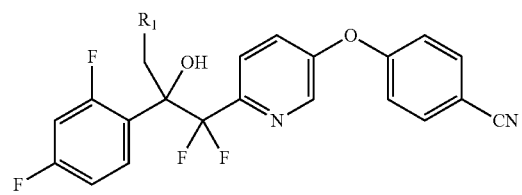

13 Claims, No Drawings

(56) References Cited

OTHER PUBLICATIONS

Extended European Search Report dated Aug. 3, 2018 in connection with EP 18177072.8.
Extended European Search Report dated Oct. 24, 2018 in connection with EP 12802997.2.
Extended European Search Report dated Oct. 15, 2018 in connection with EP 16797145.6.
International Search Report and Written Opinion dated Nov. 16, 2012 in connection with PCT/US2012/043140.
International Search Report and Written Opinion dated Nov. 16, 2012 in connection with PCT/US2012/043147.
International Search Report and Written Opinion dated Feb. 3, 2017 in connection with PCT/US2016/032877.
Baya et al; Fungicidal activity of .beta.-thujaplicin analogues; Pest Management Science, 2001;57:833-8.
Eto et al., New antifungal 1,2,4-triazoles with difluoro(heteroaryl)methyl moiety. Chem Pharm Bull (Tokyo). Jul. 2000;48(7):982-90.
Nishimura et al; Cell-associated collagenolytic activity by Candida albicans, Mycopathologia. 2001;153:125-8.
Patani et al., Bioisosterism: A Rational Approach in Drug Design. Chem Rev. Dec. 19, 1996;96(8):3147-3176.
Extended European Search Report dated May 13, 2020 in connection with EP Patent Application No. 19214854.2.
EP19214854.2, May 13, 2020, Extended European Search Report.

* cited by examiner

ANTIFUNGAL COMPOUNDS

CROSS-REFERENCE TO RELATED APPLICATIONS

This application is the National Phase under 35 U.S.C. § 371 of PCT International Application No. PCT/US2016/032877, filed May 17, 2016, which claims the priority of U.S. Provisional Patent Application No. 62/163,106, filed May 18, 2015. The entire contents of the aforementioned applications are hereby incorporated herein by reference.

INTRODUCTION

The present invention relates to antifungal compounds. The present invention also relates to processes for the preparation of these compounds, to agricultural and pharmaceutical compositions comprising them, and to their use in the treatment and control of fungal diseases or disorders, especially in agriculture.

BACKGROUND OF THE INVENTION

Fungicides are compounds, of natural or synthetic origin, which act to protect and cure plants against damage caused by agriculturally relevant fungi. Generally, no single fungicide is useful in all situations and, as a consequence, there is a need for new fungicidal agents that may have better performance, be easier to use and/or be more cost effective.

U.S. Pat. No. 8,748,461 describes a series of fungicidal compounds that function as modulators (e.g. inhibitors) of the activity of metalloenzymes. One particular compound disclosed in U.S. Pat. No. 8,748,461 is 4-(6-(2-(2,4-difluorophenyl)-1,1-difluoro-2-hydroxy-3-(1H-tetrazol-1-yl)propyl)pyridin-3-yloxy)benzonitrile (Example 5 of U.S. Pat. No. 8,748,461), the structure of which is shown below.

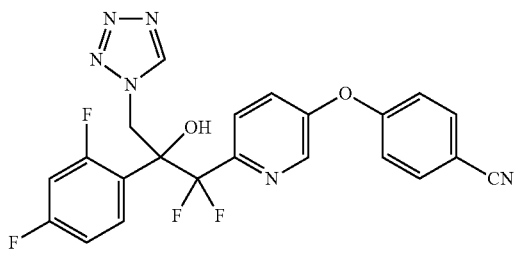 [SMILES: N#Cc1ccc(Oc2ccc(C(F)(F)C(O)(Cn3cnnn3)c3ccc(F)cc3F)nc2)cc1]

Example 5 of U.S. Pat. No. 8,748,461

Despite the promising compounds described in U.S. Pat. No. 8,748,461, there still remains a need for antifungal compounds that demonstrate improved fungicidal activity against agriculturally relevant fungi (for example, improved fungicidal activity against leaf blotch of wheat caused by *Septoria tritici*).

In addition, there is a need for antifungal compounds that possess favourable physicochemical properties (for example, good water solubility and a favourable partition coefficient (Log D) value).

It is therefore an objective of the present invention to provide compounds that address one or more of the foregoing needs.

SUMMARY OF THE INVENTION

In one aspect, the present invention provides a compound of Formula (I):

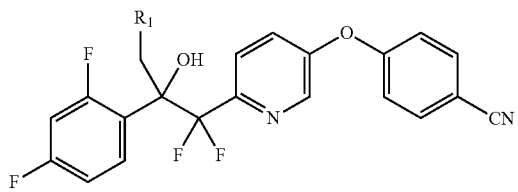

wherein $R_1$ is a group selected from one of Formulae (II) or (III) shown below:

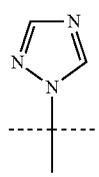

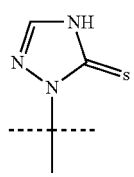

or an acceptable salt, solvate or hydrate thereof.

In another aspect, the present invention provides an agricultural composition comprising a compound of Formula (I) as defined herein, or an acceptable salt, solvate or hydrate thereof, and one or more agriculturally acceptable excipients.

In another aspect, the present invention provides a compound of Formula (I) as defined herein, or an acceptable salt, solvate or hydrate thereof, or an agricultural composition as defined herein, for use in treatment or prevention of a metalloenzyme-mediated disease or disorder. Suitably, the compounds of Formula (I) are for use in the treatment or prevention of a metalloenzyme-mediated disease or disorder in or on a plant.

In another aspect, the present invention provides the use of a compound of Formula (I) as defined herein, or an acceptable salt, solvate or hydrate thereof, or an agricultural composition as defined herein, for the treatment or prevention of a metalloenzyme-mediated disease or disorder. Suitably, the compounds of Formula (I) are for use in the treatment or prevention of a metalloenzyme-mediated disease or disorder in or on a plant.

In another aspect, the present invention provides a method of treating or preventing a metalloenzyme-mediated disease or disorder, said method comprising administering an effective amount of a compound of Formula (I) as defined herein, or an acceptable salt, solvate or hydrate thereof, or an agricultural composition as defined herein. Suitably, the method is a method of treating or preventing a metalloenzyme-mediated disease or disorder in or on a plant.

In another aspect, the present invention provides a compound of Formula (I) as defined herein, or an acceptable salt, solvate or hydrate thereof, or an agricultural composition as defined herein, for use in the treatment or prevention of fungal diseases or disorders. Suitably, the compounds of Formula (I) are for use in the treatment or prevention of fungal diseases or disorder in or on a plant.

In another aspect, the present invention provides the use of a compound of Formula (I) as defined herein, or an acceptable salt, solvate or hydrate thereof, or an agricultural composition as defined herein, for use in the treatment or prevention of fungal diseases or disorders. Suitably, the use of a compound of Formula (I) is in the treatment or prevention of fungal diseases or disorder in or on a plant.

In another aspect, the present invention provides a method of treating or preventing a fungal disease or disorder, said method comprising the administration of an effective amount of a compound of Formula (I) as defined herein, or an acceptable salt, solvate or hydrate thereof, or an agricultural composition as defined herein. Suitably, the method is a method of treating or preventing a fungal disease or disorder in or on a plant.

In another aspect, the present invention provides a compound of Formula (I) as defined herein, or an acceptable salt, solvate or hydrate thereof, or an agricultural composition as defined herein, for use in inhibiting metalloenzyme activity. Suitably, the compound of formula (I) is for use in inhibiting metalloenzyme activity in a fungal cell residing in or on a plant.

In another aspect, the present invention provides the use of a compound of Formula (I) as defined herein, or an acceptable salt, solvate or hydrate thereof, or an agricultural composition as defined herein, for inhibiting metalloenzyme activity. Suitably, the use of a compound of formula (I) is for inhibiting metalloenzyme activity in a fungal cell residing in or on a plant.

In another aspect, the present invention provides a method of inhibiting metalloenzyme activity in or on a plant, the method comprising the administration of an effective amount of a compound of Formula (I) as defined herein, or an acceptable salt, solvate or hydrate thereof, or an agricultural composition as defined herein. Suitably, the method is a method of inhibiting metalloenzyme activity in a fungal cell residing in or on a plant.

In another aspect, the present invention provides a compound of Formula (I) as defined herein, or an acceptable salt, solvate or hydrate thereof, or an agricultural composition as defined herein, for use in inhibiting lanosterol demethylase (CYP51) activity. Suitably, the compound of formula (I) is for use in inhibiting lanosterol demethylase (CYP51) activity in a fungal cell residing in or on a plant.

In another aspect, the present invention provides the use of a compound of Formula (I) as defined herein, or an acceptable salt, solvate or hydrate thereof, or an agricultural composition as defined herein, for inhibiting lanosterol demethylase (CYP51) activity. Suitably, the use of a compound of formula (I) is for inhibiting lanosterol demethylase (CYP51) activity in a fungal cell residing in or on a plant.

In another aspect, the present invention provides a method of inhibiting lanosterol demethylase (CYP51) activity in or on a plant, the method comprising the administration of an effective amount of a compound of Formula (I) as defined herein, or an acceptable salt, solvate or hydrate thereof, or an agricultural composition as defined herein. Suitably, the method is a method of inhibiting lanosterol demethylase (CYP51) activity in a fungal cell residing in or on a plant.

In another aspect, the present invention provides a pharmaceutical composition comprising a compound of Formula (I) as defined herein, or a pharmaceutically acceptable salt, solvate, prodrug or hydrate thereof, and one or more pharmaceutically acceptable excipients.

In another aspect, the present invention provides a compound of Formula (I) as defined herein, or an acceptable salt, solvate, prodrug or hydrate thereof, or a pharmaceutical composition as defined herein, for use in therapy.

In another aspect, the present invention provides a pharmaceutical composition as defined herein, for use in treatment or prevention of a metalloenzyme-mediated disease or disorder.

In another aspect, the present invention provides a method of treating or preventing a metalloenzyme-mediated disease or disorder, said method comprising administering an effective amount of a pharmaceutical composition as defined herein.

In another aspect, the present invention provides a pharmaceutical composition as defined herein, for use in the treatment or prevention of diseases caused by fungal pathogens.

In another aspect, the present invention provides a method of treating or preventing diseases caused by fungal pathogens, said method comprising the administration of an effective amount of a pharmaceutical composition as defined herein.

In another aspect, the present invention provides a compound of Formula (I) as defined herein, or an acceptable salt, solvate, prodrug or hydrate thereof, or a pharmaceutical composition as defined herein, for use in inhibiting metalloenzyme activity in or on a human or animal subject.

In another aspect, the present invention provides the use of a compound of Formula (I) as defined herein, or an acceptable salt, solvate, prodrug or hydrate thereof, or a pharmaceutical composition as defined herein, for inhibiting metalloenzyme activity in or on a human or animal subject.

In another aspect, the present invention provides a method of inhibiting metalloenzyme activity in or on a human or animal subject, the method comprising the administration of an effective amount of a compound of Formula (I) as defined herein, or an acceptable salt, solvate, prodrug or hydrate thereof, or a pharmaceutical composition as defined herein.

The present invention further provides a method of synthesizing a compound, or an acceptable salt, solvate, prodrug or hydrate thereof, as defined herein.

In another aspect, the present invention provides a compound, or an acceptable salt, solvate, prodrug or hydrate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

The term "administration" or "administering" includes routes of introducing the compound(s) to the plant to perform their intended function.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated", "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "therapeutically or agriculturally effective amount" refers to that amount of the compound being administered sufficient to prevent development of or alleviate to some extent one or more of the symptoms of the condition or disorder being treated.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of a metalloenzyme, as compared to the activity of a metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

References to "compounds of the invention" or "compounds described herein" are used interchangeably to refer to compounds of Formula I defined herein.

Compounds of the Invention

As previously stated, in one aspect, the present invention provides a compound of Formula (I) shown below:

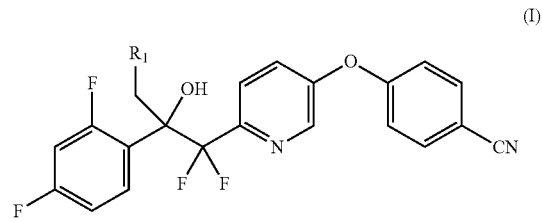

wherein $R_1$ is a group selected from one of Formulae (II) or (III) shown below:

or an acceptable salt, solvate, prodrug or hydrate thereof.

In the definition of the $R_1$ group above, the symbol ----- denotes the point attachment of the $R_1$ group to the —$CH_2$— group in the compound of formula (I) shown above.

In an embodiment, the $R_1$ group is a group of Formula (II), i.e. the compound is: 4-((6-(2-(2,4-difluorophenyl)-1,1-difluoro-2-hydroxy-3-(1H-1,2,4-triazol-1-yl)propyl)pyridin-3-yl)oxy)benzonitrile, or an acceptable salt, solvate, prodrug or hydrate thereof.

In an embodiment, the $R_1$ group is a group of Formula (III), i.e. the compound is: 4-((6-(2-(2,4-difluorophenyl)-1,1-difluoro-2-hydroxy-3-(5-thioxo-4,5-dihydro-1H-1,2,4-triazol-1-yl)propyl)pyridin-3-yl)oxy)benzonitrile, or an acceptable salt, solvate, prodrug or hydrate thereof.

In comparison with the compound of example 5 described in U.S. Pat. No. 8,748,461, (4-(6-(2-(2,4-difluorophenyl)-1,1-difluoro-2-hydroxy-3-(1H-tetrazol-1-yl)propyl)pyridin-3-yloxy)benzonitile), the compounds described in Examples 1 and 2 of the present invention demonstrate improved fungicidal activity against the fungi responsible for leaf blotch of wheat (Septoria tritici).

In addition, the compounds of the present invention possess good water solubility and favourable partition coefficient (Log D) values.

The compounds of the invention may also contain linkages (e.g. carbon-carbon bonds) wherein bond rotation is restricted about that particular linkage, e.g. restriction resulting from the presence of a ring or a double bond. Accordingly, any cis/trans and E/Z isomers are expressly included in the present invention.

The compounds of the invention may also be present in multiple tautomeric forms. Where one or more tautomeric forms exist, the invention expressly includes all such tautomeric forms of the compounds described herein, even though only a single tautomeric form may be represented. For example, compounds of the invention in which $R_1$ is of Formula (III) may exist in different tautomeric forms and references to compounds of the invention include all such forms. The tautomeric forms of the compound in which $R_1$ is of formula (III) are shown in Formulae (IV) and (V) shown below.

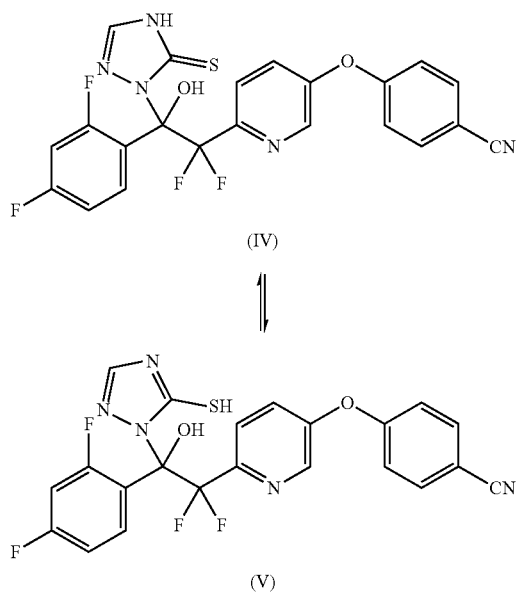 [SMILES: N#Cc1ccc(Oc2ccc(C(F)(F)C(O)(c3ccc(F)cc3F)n3nc[nH]c3=S)nc2)cc1 ; "(IV)" ; N#Cc1ccc(Oc2ccc(C(F)(F)C(O)(c3ccc(F)cc3F)n3ncnc3S)nc2)cc1 ; "(V)"]

The compounds of the present invention may exist in one or more isomeric forms. All isomeric forms of the compounds of the invention are expressly included in the present invention.

The term "isomers" or "isomeric forms" is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, a single enantiomer or diastereomer of a chiral compound of the invention is preferred in treating a disease on a plant.

The compounds of the present invention may exist in one or more crystalline or polymorphic forms. All crystaline forms and polymorphs of the compounds of the invention are expressly included in the present invention.

The present invention also encompasses extracts and fractions comprising compounds of the invention.

A suitable acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid.

It is also to be understood that certain compounds of the invention may exist in solvated as well as unsolvated forms such as, for example, hydrated forms. It is to be understood that the invention encompasses all such solvated forms that possess fungicidal activity.

Compounds of the invention containing a suitable amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a prodrug which is broken down (e.g. in the fungal cell or plant) to release a compound of the present invention. A prodrug form may be desirable in order to alter the physical properties and/or the pharmacokinetic properties of a compound of the invention. A prodrug can be formed when the compound of the invention contains a suitable group or substituent to which a property-modifying group can be attached.

Accordingly, the present invention includes those compounds of Formula (I) as defined hereinbefore when made available by organic synthesis and when made available by way of cleavage of a prodrug thereof. Accordingly, the present invention includes those compounds of the formula (I) that are produced by organic synthetic means and also such compounds that are produced (e.g. in a fungal cell or plant) by way of metabolism of a precursor compound, that is a compound of the formula (I) may be a synthetically-produced compound or a metabolically-produced compound.

Various forms of prodrug have been described, for example in the following documents:
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

Synthesis

The present invention further provides a method of synthesizing a compound, or an acceptable salt or solvate thereof, as defined herein.

In another aspect, the present invention provides a compound, or an acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Compounds of the invention can be made by any suitable means known in the art of organic synthesis. For example, a person skilled in the art will be able to synthesize the compound by following the examples described herein and/or by appropriate adaptation of the synthetic techniques described in U.S. Pat. No. 8,748,461.

Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ *Edition*, Carlson R, Ed, 2005; Elsevier Science Ltd.; Jähnisch, K et al., *Angew. Chem. Int. Ed. Engl.* 2004, 43, 406; and references therein). Additional reaction schemes and protocols may be determined by the skilled artisan by use of commercially available structure-searchable database software, for instance, SciFinder® (Chemical Abstracts Service (CAS®) division of the American Chemical Society) and CrossFire Beilstein® (Elsevier MDL), or by appropriate keyword searching using an internet search engine such as Google® or keyword databases such as the US Patent and Trademark Office text database.

It is also to be understood that all reaction conditions described in the accompanying examples, including choice of solvent, reaction atmosphere, reaction temperature, duration of the experiment and workup procedures, can be modified or adapted as appropriate by a person skilled in the art.

It is also understood by one skilled in the art of organic synthesis that the functionality present on various portions of the molecule must be compatible with the reagents and reaction conditions utilised.

Necessary starting materials may be obtained commercially or by standard procedures of organic chemistry. The preparation of relevant starting materials is described in the accompanying Example section. Alternatively, necessary starting materials are obtainable by analogous procedures to those illustrated which are within the ordinary skill of an organic chemist.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if certain reactants include, for example, groups such as amino, carboxy or hydroxy it may be desirable to protect the group in some of the reactions mentioned herein.

Suitable acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids can be useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases can be useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art.

Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In a particular aspect, the present invention provides a process for synthesising a compound of Formula (I) in which R$_1$ is a group of Formula (II), the process comprising contacting a compound of Formula D:

D

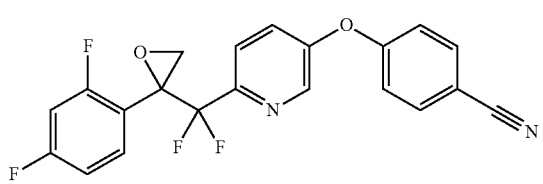

with 1H-1,2,4-triazole in the presence of a base and a suitable solvent.

Any suitable base may be used in the reaction. In an embodiment, the base is potassium carbonate.

Any suitable solvent may be used in the reaction. In an embodiment, the solvent is dimethylsulfoxide.

A person skilled in the art will be able to select a suitable temperature to use for this reaction. In an embodiment, the reaction is carried out at a temperature within the range of 15 to 60° C.

Suitably the reaction is carried out in an inert atmosphere.

Compounds of Formula D can be prepared by the procedures described in Example 1 herein.

In another aspect, the present invention provides a process for synthesising a compound of Formula (I) in which $R_1$ is a group of Formula (III), the process comprising contacting a compound of Formula 1 shown below:

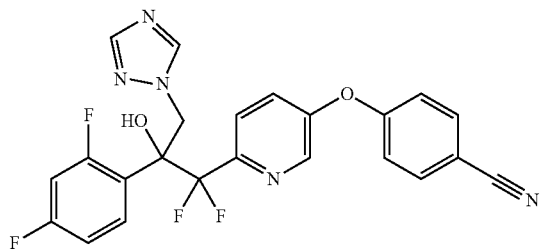

1 with sulfur in the presence of a suitable solvent.

Any suitable solvent may be used in the reaction. In an embodiment, the solvent is N-methyl-2-pyrrolidinone.

A person skilled in the art will be able to select a suitable temperature to use in this reaction. In an embodiment, the reaction is carried out at a temperature within the range of 50 to 200° C.

Suitably the reaction is carried out in an inert atmosphere.

Agricultural Compositions

Compounds of Formula (I) may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of a non-limiting example, an acid function can form salts including those derived from alkali or alkaline earth metals and those derived from ammonia and amines. Examples of preferred cations include sodium, potassium, and magnesium.

Compounds of Formula (I) may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Suitable salts include those derived from alkali or alkaline earth metals and those derived from ammonia and amines. Preferred cations include sodium, potassium, magnesium, and aminium cations of the formula:

$R^9R^{10}R^{11}R^{12}N^+$ wherein $R^9$, $R^{10}$, $R^{11}$ and $R^{12}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^9$, $R^{10}$, $R^{11}$ and $R^{12}$ are sterically compatible. Additionally, any two of $R^9$, $R^{10}$, $R^{11}$ and $R^{12}$ together may represent an aliphatic difunctional moiety containing one to twelve carbon atoms and up to two oxygen or sulfur atoms.

Salts of the compounds of Formula (I) can be prepared by treatment of compounds of Formula (I) with a metal hydroxide, such as sodium hydroxide, with an amine, such as ammonia, trimethylamine, diethanolamine, 2-methyl-thiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of Formula (I) because they are water-soluble and lend themselves to the preparation of desirable aqueous based herbicidal compositions.

Preferably, the compounds of the present disclosure are applied in the form of an agricultural composition or formulation, comprising one or more of the compounds of Formula (I), or a salt, solvate or hydrate thereof, with an agriculturally or phytologically acceptable excipient or carrier.

The compositions comprising compounds of the present invention can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The present disclosure contemplates all vehicles by which one or more of the compounds may be formulated for delivery and use as a fungicide. Typically, formulations are applied as aqueous suspensions or emulsions. Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Wettable powders, which may be compacted to form water dispersible granules, comprise an intimate mixture of one or more of the compounds of Formula (I), an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds of the present invention can be formulated as ordinary tablets, capsules, solids, liquids, emulsions, slurries, oils, fine granules or powders, which are suitable for administration to plants, fields or other agricultural areas. In preferred embodiments, the preparation comprises between 1 and 95% (e.g., 1, 2, 3, 4, 5, 6, 7, 8, 9, 10, 25%, 75%, 80%, 90%, 95%) of a compound of the present invention in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound of the present invention is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound of the present invention. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound of the present invention is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Emulsifiable concentrates of the compounds of Formula (I) may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula (I), dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula (I) can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound of the present invention or combinations or derivatives thereof) useful in the prevention or treatment of a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cottonseed, walnut, palm, castor, earth almond, hazelnut, avocado, sesame, croton tiglium, cacao, linseed, rapeseed, and canola oils and their hydrogenated derivatives); petroleum derived oils (e.g., parafins and petroleum jelly), and other water immiscible hydrocarbons (e.g., parafins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodium carboxymethylcellulose, ethyl cellulose, hydroxypropyl methyl cellulose, and mixtures thereof.

Dusts containing the compounds of Formula (I) may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-016) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula (I) and the pesticidal compound in the combination can generally be present in a weight ratio of from 1:100 to 100:1.

Agricultural Applications and Uses

The present invention further relates to the use of the compounds and agricultural compositions defined herein in the treatment or prevention of a metalloenzyme-mediated disorder or disease, especially in agricultural or agrarian settings.

Thus, the present invention provides a compound of Formula (I) as defined herein, or an acceptable salt, solvate or hydrate thereof, or an agricultural composition as defined herein, for use in treatment or prevention of a metalloenzyme-mediated disease or disorder. Suitably, the compounds of Formula (I) are for use in the treatment or prevention of a metalloenzyme-mediated disease or disorder in or on a plant.

In another aspect, the present invention provides the use of a compound of Formula (I) as defined herein, or an acceptable salt, solvate or hydrate thereof, or an agricultural composition as defined herein, for the treatment or prevention of a metalloenzyme-mediated disease or disorder. Suitably, the compounds of Formula (I) are for use in the treatment or prevention of a metalloenzyme-mediated disease or disorder in or on a plant.

In another aspect, the present invention provides a method of treating or preventing a metalloenzyme-mediated disease or disorder, said method comprising administering an effective amount of a compound of Formula (I) as defined herein, or an acceptable salt, solvate or hydrate thereof, or an agricultural composition as defined herein. Suitably, the method is a method of treating or preventing a metalloenzyme-mediated disease or disorder in or on a plant The compounds and compositions of the present invention can be used in methods of modulating metalloenzyme activity in a microorganism on a plant comprising contacting a compound of the present invention with the plant (e.g., seed, seedling, grass, weed, grain). The compounds and compositions of the present invention can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence of the fungi concerned. The administration can be either as a treatment or preventative regimen.

One aspect is a method of treating or preventing a fungal disease or disorder in or on a plant comprising contacting a compound (or composition) of the present invention with the plant. Another aspect is a method of treating or preventing fungi growth in or on a plant comprising contacting a compound (or composition) of the present invention with the plant. Another aspect is a method of inhibiting microorganisms in or on a plant comprising contacting a compound (or composition) of the present invention with the plant.

The compounds and compositions of the present invention may be used in methods of preventing or controlling pathogen induced diseases on a plant comprising contacting a compound of the present invention with the plant (e.g., seed, seedling, grass, weed, grain) or an area adjacent to the plant. The compounds and compositions herein may be used to treat a plant, field or other agricultural area by administering the compound or composition (e.g., contacting, applying, spraying, atomizing, dusting, etc.) to the subject plant, field or other agricultural area. The administration may be either pre- or post-emergence. The administration may be either as a treatment or preventative regimen. As such, the compounds, compositions and agricultural uses herein include lawn, turf, ornamental vegetation, home and garden, farming, range and pasture applications. The pathogen may be any on a plant and include those delineated herein.

One embodiment of the present disclosure is a use of a compound of Formula (I), for protection of a plant against attack by a phytopathogenic organism or the treatment of a plant infested by a phytopathogenic organism, comprising the application of a compound of Formula (I), or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula (I) and a phytologically acceptable carrier material.

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula (I). The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

The compositions of Forumla (I) may be effective against pathogen induced diseases where the plant fungal pathogen belonging to at least one genera selected from *Blumeria*, *Podosphaera*, *Sphaerotheca*, *Uncinula*, *Erysiphe*, *Puccinia*, *Phakopsora*, *Gymnosporangium*, *Hemileia*, *Uromyces*, *Alternaria*, *Cercospora*, *Cladosporium*, *Cochliobolus*, *Colletotrichum*, *Magnaporthe*, *Mycosphaerella*, *Phaeosphaeria*, *Pyrenophora*, *Ramularia*, *Rhyncosporium*, *Septoria*, *Venturia*, *Ustilago*, *Aspergillus*, *Penicillium*, *Drechslera*, *Fusarium*, *Botrytis*, *Gibberella*, *Rhizoctonia*, *Pseudocercosporella*, *Sclerotinia*, *Helminthosporium*, *Stagonospora*, *Exserohilum*, and *Pyricularia*. Pathogens such as *Venturia inaequalis*, *Septoria tritici*, *Cercospora beticola*, *Cercospora arachidicola*, *Colletotrichum lagenarium*, *Puccinia graminis* f. sp. *tritici*, *Uncinula necator*, *Blumeria graminis*, and *Mycosphaerella fijiensis* by be controlled by compositions of Formula (I). Additionally, the compositions of Formula (I) may be effective in preventing or controlling diseases including apple scab, speckled leaf blotch of wheat, leaf spot of sugarbeets, leaf spot of peanut, cucumber anthracnose, wheat leaf rust, grape powdery mildew, wheat powdery mildew, and black sigatoka.

The invention provides kits for the treatment or prevention of agricultural or plant disease or disorders. In one embodiment, the kit includes a composition containing an effective amount of a compound of the present invention in a form suitable for delivery to a site plant. In some embodiments, the kit comprises a container which contains a compound of the present invention as described herein (e.g., of any formulae herein); such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired, the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

The compounds of the present disclosure may be effective in use with plants in an "effective" or "disease-inhibiting and phytologically acceptable amount". The terms "effective" or "disease-inhibiting and phytologically acceptable amount" both refer to an amount of a compound or composition of the present invention that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

Combination Treatments

The compounds herein can be used alone or in combination with other agriculturally active agents. The use of the compounds or compositions (and the compositions) defined herein can therefore further comprise an additional active agent, such as, for example, an azole fungicide selected from epoxiconazole, tebuconazole, fluquinconazole, flutriafol, metconazole, myclobutanil, cycproconazole, prothioconazole and propiconazole.

Such conjoint treatment may be achieved by way of the simultaneous, sequential or separate dosing of the individual components of the treatment. Such combination products employ the compounds of this invention within the dosage range described hereinbefore and the other agriculturally-active agent within its approved dosage range.

Thus the present invention futher provides a combination suitable for use in the treatment of a fungal diseases or disorders in or on plants, comprising a compound of the invention as defined hereinbefore, or an acceptable salt, solvate or hydrate thereof, and another agriculturally-active agent.

In a further aspect of the invention there is provided a compound of the invention or an acceptable salt, solvate or hydrate thereof, for use in the treatments defined herein in combination with another agriculturally-active agent.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided an agricultural composition which comprises a compound of the invention, or a pharmaceutically acceptable salt, solvate or hydrate thereof, in combination with another agriculturally active agent, in association with an agriculturally acceptable diluent or carrier.

The use of the compounds or compositions defined herein can further comprise an additional active agent such as a fungicide selected from the group trifloxystrobin, pyraclostrobin, orysastrobin, fluoxastrobin and azoxystrobin.

The compounds of the present invention may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, laminarin, kasugamycin, kasugamycin hydrochloride hydrate, kresoxim-methyl, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulf an, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPIC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, triallate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, and xylachlor.

EXAMPLES

The present invention will now be demonstrated using specific examples that are not to be construed as limiting.

Example 1. Preparation of 4-((6-(2-(2,4-difluorophenyl)-1,1-difluoro-2-hydroxy-3-(1H-1,2,4-triazol-1-yl)propyl)pyridin-3-yl)oxy)benzonitrile (1)

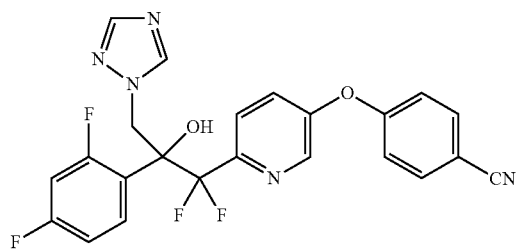

A) 4-((6-bromopyridin-3-yl)oxy)benzonitrile (A)

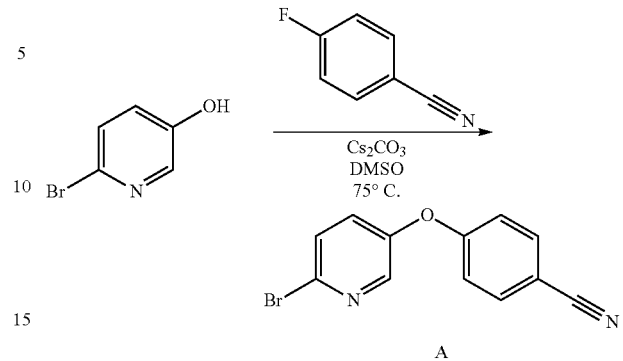

To a stirred solution of 6-bromopyridin-3-ol (5.0 g, 28.7 mmol) and 4-fluorobenzonitrile (3.48 g, 28.7 mmol) in dry DMSO (57.5 ml) under nitrogen was added cesium Carbonate (14.04 g, 43.1 mmol). The reaction mixture was stirred at 75° C. for 18 h. The reaction was poured into ice water. The pH was adjusted to make the solution just acidic (pH=6) using 1 N HCl. The resulting precipitate was filtered, washed with water, washed with a little bit of ether (started washing out product), and dried (MgSO$_4$) to give 4-((6-bromopyridin-3-yl)oxy)benzonitrile (6.292 g, 21.73 mmol, 76% yield) as a brown solid (95% purity). 1H NMR (400 MHz, CDCl3) δ 8.22 (d, J=2.9 Hz, 1H), 7.70-7.63 (m, 2H), 7.56-7.51 (m, 1H), 7.28 (dd, J=8.5, 2.9 Hz, 1H), 7.10-7.02 (m, 2H).

B) Preparation of ethyl 2-(5-(4-cyanophenoxy)pyridin-2-yl)-2,2-difluoroacetate (B)

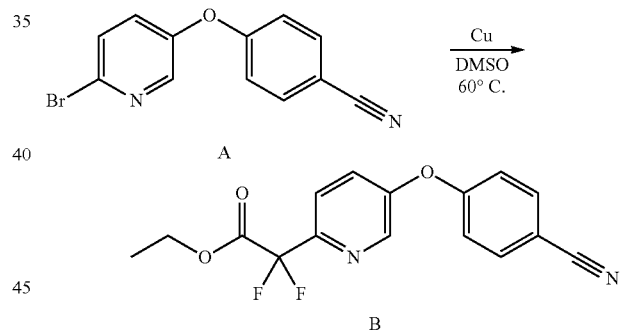

Crude benzonitrile A was dried azeotropicallty with toluene to remove any possible trace water from the starting material. A magnetically stirred mixture of ethyl 2-bromo-2,2-difluoroacetate (3.08 ml, 23.99 mmol) and copper (2.98 g, 46.9 mmol) in dry DMSO (33.7 ml) was stirred for 1 h at rt, then 4-((6-bromopyridin-3-yl)oxy)benzonitrile (5.57 g, 20.25 mmol) was added in one portion. The reaction mixture was stirred at 60° C. for 3 days. Rxn complete by TLC. Removed heat, diluted with 100 mL EtOAc and stirred for 20 minutes. Filtered through a plug of Celite, washing with EtOAc. The filtrate was washed 3× with saturated NH$_4$Cl to remove any remaining copper. Solution was dried and solvent was removed under reduced pressure to produce crude desired product as brown oil (5.95 g; ~90% purity; 83% yield). The residue was chromatographed (0-20% EtOAc/hexanes) to give ethyl 2-(5-(4-cyanophenoxy)pyridin-2-yl)-2,2-difluoroacetate B (3.897 g, 12.12 mmol, 59.9% yield) as a clear oil. $^1$H NMR (300 MHz, CDCl3) δ 8.44 (d, J=2.7 Hz, 1H), 7.78 (d, J=8.7 Hz, 1H), 7.73-7.64 (m, 2H), 7.49 (dd, J=8.6, 2.7 Hz, 1H), 7.16-7.07 (m, 2H), 4.39 (q, J=7.1 Hz, 2H), 1.35 (t, J=7.2 Hz, 3H).

C) Preparation of 4-((6-(2-(2,4-difluorophenyl)-1,1-difluoro-2-oxoethyl)pyridin-3-yl)-oxy)benzonitrile (C)

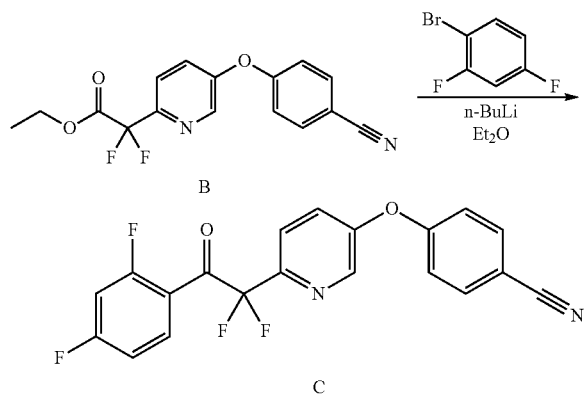

To a magnetically stirred mixture of 1-bromo-2,4-difluorobenzene (0.923 ml, 8.17 mmol) in Et$_2$O (20.95 ml) under N$_2$ atmosphere at −78° C. was added slowly 2.5 M N-butyl lithium (3.27 ml, 8.17 mmol) in hexanes. After completion of addition, ethyl 2-(5-(4-cyanophenoxy)pyridin-2-yl)-2,2-difluoroacetate B (2.00 g, 6.28 mmol) in Et$_2$O (15 mL) was added and the reaction was stirred at −60 to −50° C. for 1 hour. The reaction was quenched with 2N HCl until reaction mixture was acidic. The reaction was allowed to warm to rt and the mixture was then made basic with sat. aq. NaHCO$_3$. The layers were separated and the aqueous layer was extracted with Et$_2$O. The combined orangic phases were dried (MgSO$_4$) and concentrated. The crude product was dried on the rotavap under vacuum for 4 hours to give 4-((6-(2-(2,4-difluorophenyl)-1,1-difluoro-2-oxoethyl)pyridin-3-yl)oxy)benzonitrile C (2.515 g, 5.53 mmol, 88%) (85% purity) as a yellow oil, which was used in the next step without further purification. $^1$H NMR (300 MHz, CDCl$_3$) δ 8.36 (d, J=2.7 Hz, 1H), 8.15-8.02 (m, 1H), 7.86 (d, J=8.7 Hz, 1H), 7.74-7.65 (m, 2H), 7.53 (dd, J=8.6, 2.7 Hz, 1H), 7.16-7.06 (m, 2H), 7.05-6.96 (m, 1H), 6.84 (ddd, J=10.9, 8.6, 2.4 Hz, 1H).

D) Preparation of 4-((6-((2-(2,4-difluorophenyl)oxiran-2-yl)difluoromethyl)pyridin-3-yl)-oxy)benzonitrile (D)

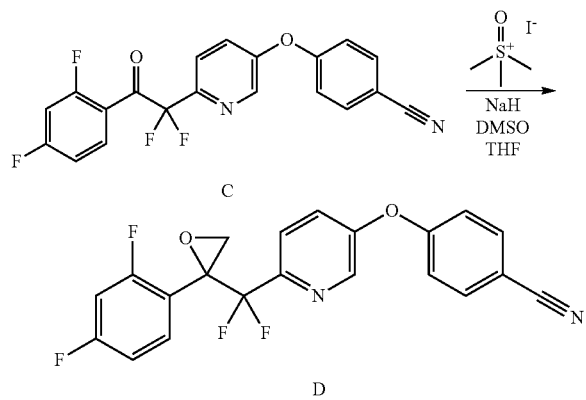

To a magnetically stirred solution of trimethylsulfoxonium iodide (1.574 g, 7.15 mmol) in dry THF/DMSO (1:1, 18 mL each) was added sodium hydride (0.286 g, 7.15 mmol) under N$_2$ atmosphere. The reaction mixture was stirred at rt for 1 h, then cooled to 0° C. 4-((6-(2-(2,4-difluorophenyl)-1,1-difluoro-2-oxoethyl)pyridin-3-yl)oxy)benzonitrile C (2.500 g, 5.50 mmol) in THF (18 mL) was added slowly to maintain the temperature below 1.5° C. (~1-1.5° C.; internal temperature probe). The reaction was maintained at 0° C. for 30 min (TLC indicated complete conversion to product), and saturated sodium bicarbonate was added to quench. Brine was added and the mixture was extracted with Et$_2$O. The combined organic phases were diluted with hexanes and washed with brine (2×) and water (1×), dried (MgSO$_4$) and concentrated to give a milky amber oil. $^1$H-NMR of the crude reaction mixture indicated ~90% purity. Chromatographed on silica (0-10% EtOAc/hexanes) to give 4-((6-((2-(2,4-difluorophenyl)-oxiran-2-yl)difluoromethyl)pyridin-3-yl)oxy)benzonitrile D (1.789 g, 4.47 mmol, 81% yield) as a white solid. $^1$H NMR (300 MHz, CDCl3) δ 8.46 (d, J=2.7 Hz, 1H), 7.73-7.62 (m, 2H), 7.52 (dd, J=8.6, 0.6 Hz, 1H), 7.48-7.35 (m, 2H), 7.13-7.02 (m, 2H), 6.92-6.80 (m, 1H), 6.75 (ddd, J=10.0, 8.9, 2.5 Hz, 1H), 3.46 (d, J=5.1 Hz, 1H), 3.03-2.96 (m, 1H).

E) Preparation of 4-((6-(2-(2,4-difluorophenyl)-1,1-difluoro-2-hydroxy-3-(1H-1,2,4-triazol-1-yl)propyl)pyridin-3-yl)oxy)benzonitrile (1)

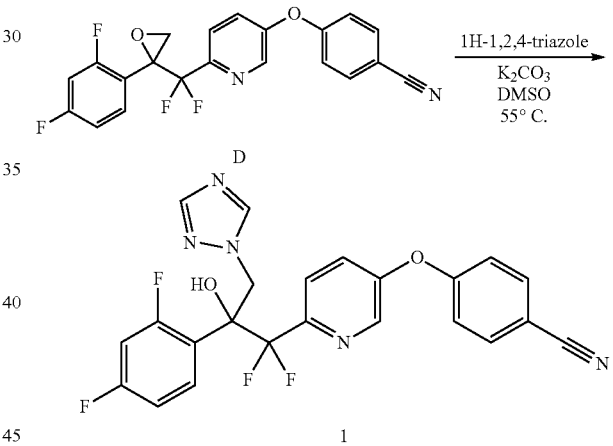

To a magnetically stirred mixture of 4-((6-((2-(2,4-difluorophenyl)oxiran-2-yl)difluoromethyl)pyridin-3-yl)oxy)benzonitrile D (77 mg, 0.192 mmol) in dry DMSO (1.923 mL) was added 1H-1,2,4-triazole (39.9 mg, 0.577 mmol) and K$_2$CO$_3$ (133 mg, 0.962 mmol) in a dry 25 mL vial under N$_2$ atmosphere. The reaction mixture was stirred at 55° C. for 16 hours, cooled to RT and diluted with ice-water. The pH was adjusted to neutral with 2N HCl and the mixture extracted with DCM (2×). The combined organic extracts were filtered through a Phase Separator and evaporated. The crude material was purified on silica (ISCO, 24 gram column, gradient to 70% EA/Hex over 20 min) to afford 68 mg (71.6%) of the title compound 1 as a off-white resin. $^1$H NMR (400 MHz, CDCl$_3$) δ 8.36 (d, J=2.6 Hz, 1H), 8.14 (s, 1H), 7.74 (s, 1H), 7.73-7.67 (m, 2H), 7.62-7.56 (m, 1H), 7.50-7.44 (m, 1H), 7.41 (dd, J=8.8, 2.8 Hz, 1H), 7.13-7.04 (m, 2H), 6.76 (ddd, J=13.9, 8.0, 5.1 Hz, 2H), 6.23 (s, 1H), 5.39 (d, J=14.3 Hz, 1H), 4.87 (d, J=14.7 Hz, 1H). $^{19}$F NMR (376 MHz, CDCl3) δ −105.22−−105.54 (m), −107.11 (d, J=19.1 Hz), −107.79 (d, J=19.1 Hz), −108.45−−108.72 (m), −109.27 (d, J=26.2 Hz). ESIMS m/z 470.4 ([M+H]+).

Example 2. Preparation of 4-((6-(2-(2,4-difluorophenyl)-1,1-difluoro-2-hydroxy-3-(5-thioxo-4,5-dihydro-1H-1,2,4-triazol-1-yl)propyl)pyridin-3-yl)oxy)benzonitrile (2)

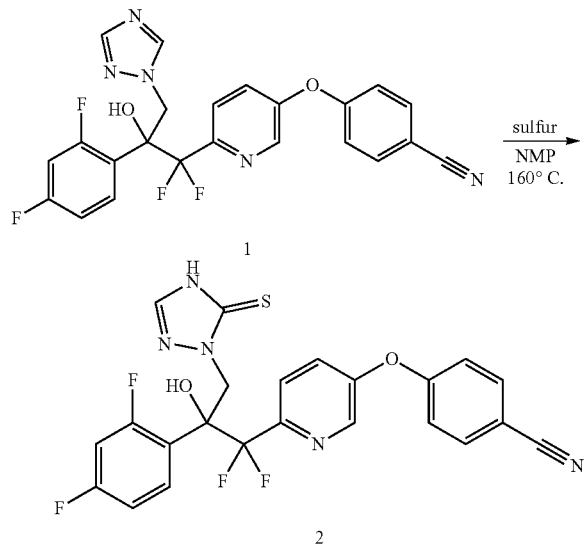

To a magnetically stirred mixture of 4-((6-(2-(2,4-difluorophenyl)-1,1-difluoro-2-hydroxy-3-(1H-1,2,4-triazol-1-yl)propyl)pyridin-3-yl)oxy)benzonitrile 1 (500 mg, 1.065 mmol) in dry N-methyl-2-pyrrolidinone (5.326 mL) was added elemental sulfur (342 mg, 10.65 mmol) in a dry 50 mL round-bottomed flask under $N_2$ atmosphere. The reaction mixture was stirred at 160° C. (external temp monitoring) for 1 hour when the temperature was reduced to 140° C. as the reaction mixture appeared to be refluxing. TLC indicated the SM had been consumed. The reaction mixture was cooled to RT and poured into ice and diluted with water and EtOAc. The dark biphasic mixture was filtered through a pad of Celite and the layers were separated. The organic extract was dried over sodium sulfate and filtered through a Phase Separator and evaporated. The crude material was loaded onto a 25 gram silica dry-load cartridge and was purified on silica (ISCO, 40 gram column, 10% EA/Hex for 5 min, then gradient to 50% EA/Hex over 15 min, hold) which afforded insufficiently pure product material. A second column was run (ISCO, 40 gram, 35% isocratic EA/Hex), which did not sufficiently resolve the impurities from the desired product. By TLC, several plate elutions (5×10 cm plate, 40% EA/Hex) were required to identify 2 close-running spots. Several elution solvent systems were attempted, 35% ether/DCM appeared to give the best resolution of the components. The material was checked by 2D-TLC in this solvent system and the major product appeared stable to silica by this analysis. A third column (ISCO, 40 gram, 33% isocratic ether/DCM) was performed which sufficiently resolved the impurities from the desired product, affording 197 mg (35.0%) of the title compound 2 as a beige solid. $^1$H NMR (400 MHz, CDCl$_3$) δ 11.59 (s, 1H), 8.48 (d, J=2.4 Hz, 1H), 7.71-7.66 (m, 2H), 7.65 (s, 1H), 7.56 (d, J=8.7 Hz, 1H), 7.49-7.37 (m, 2H), 7.07 (d, J=8.7 Hz, 2H), 6.85-6.67 (m, 2H), 5.96 (s, 1H), 5.28 (dd, J=17.4, 2.5 Hz, 2H). $^{13}$C NMR (126 MHz, CDCl$_3$) δ 164.39, 164.29, 162.39, 162.29, 161.11, 161.01, 159.57, 159.10, 159.01, 153.06, 148.08, 147.85, 147.62, 140.77, 134.56, 131.88, 131.84, 131.80, 131.76, 127.15, 123.81, 119.39, 119.37, 119.30, 119.27, 119.20, 118.90, 118.21, 111.10, 110.94, 107.96, 104.54, 104.34, 104.31, 104.11, 51.37, 30.96. ESIMS m/z 502.5 ([M+H]+).

Example 3: Evaluation of Fungicidal Activity: Leaf Blotch of Wheat (*Mycosphaerella graminicola*; Anamorph: *Septoria tritici*; Bayer code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Using the procedure described above, the following compounds were tested:

TABLE 1

Structures of compounds tested

| Compound | Structure |
|---|---|
| Example 1 | 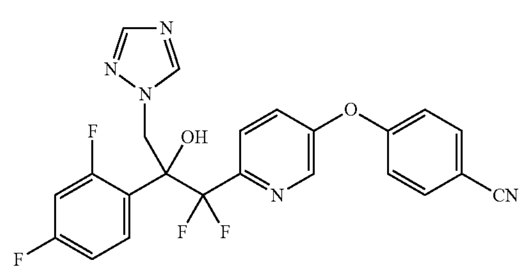 [SMILES: N#Cc1ccc(Oc2ccc(C(F)(F)C(O)(Cn3cncn3)c3ccc(F)cc3F)nc2)cc1] |

TABLE 1-continued

Structures of compounds tested

| Compound | Structure |
|---|---|
| Eaxmple 2 | (structure) |
| Comparator: Example 5 of U.S. Pat. No. 8,748,461 | (structure) |
| Comparator: Example 45 of U.S. Pat. No. 8,748,461 | (structure) |

Results:
The results obtained are shown in Table 2 below.

TABLE 2

Biological Activity-Disease Control of Septoria tritici (SEPTTR)

| | 3DP % Control | | | | 3DC % control | | | |
|---|---|---|---|---|---|---|---|---|
| Compound | 100 g/ha | 25 g/ha | 6.25 g/ha | 1.56 g/ha | 100 g/ha | 25 g/ha | 6.25 g/ha | g/ha |
| 1 | 100 | 96 | 96 | 96 | 100 | 100 | 100 | 99 |
| 2 | 100 | 100 | 98 | 94 | 100 | 99 | 94 | 80 |
| Example 5* | 64 | 50 | 36 | 22 | 58 | 47 | 34 | 22 |
| Example 45* | 95 | 93 | 89 | 58 | 86 | 85 | 86 | 78 |

*Examples from U.S. Pat. No. 8,748,461

The compounds of the present invention demonstrate improved disease control in comparison with the compounds of Example 5 and Example 45 of U.S. Pat. No. 8,748,461.

Example 4: Evaluation of Physicochemcial Properties: H$_2$O Solubility and Partition Coefficient (Log D)

The thermodynamic water solubility of the compounds shown in Table 1 above was measured.
The Log D partition coefficient was measured using the CHI method.
Results:
The results are shown in Table 3 below.

TABLE 3

Physical Properties of Selected Compounds

| Compound | H2O solubility (ppm) (thermodynamic) | LogD (CHI Method) |
|---|---|---|
| Eaxmple 1 | 37.33 | 2.90 |
| Example 2 | 23.04 | 2.83 |
| Example 5* | 28.39 | 3.02 |
| Example 45* | 5.15 | 3.32 |

*Examples from U.S. Pat. No. 8,748,461

The invention claimed is:

1. A compound of formula:

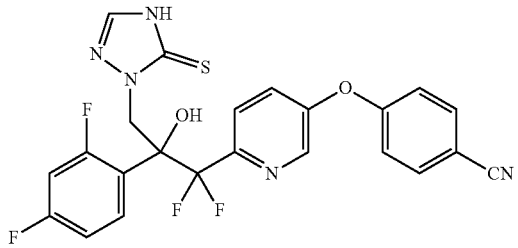 [SMILES: N#Cc1ccc(Oc2ccc(C(F)(F)C(O)(Cn3nc[nH]c3=S)c3ccc(F)cc3F)nc2)cc1]

or an agriculturally or pharmaceutically acceptable salt, solvate or hydrate thereof.

2. A compound according to claim 1, wherein the compound is:

4-((6-(2-(2,4-difluorophenyl)-1,1-difluoro-2-hydroxy-3-(5-thioxo-4,5-dihydro-1H-1,2,4-triazol-1-yl)propyl)pyridin-3-yl)oxy)benzonitrile.

3. An agricultural composition comprising a compound according to claim 1, or an agriculturally or pharmaceutically acceptable salt, solvate or hydrate thereof, and one or more agriculturally or phytologically acceptable excipients.

4. A method for the treatment of a metalloenzyme-mediated disease or disorder in a plant comprising applying to the plant a compound according to claim 1, or an agricultural composition according to claim 3.

5. The method according to claim 4, wherein the metalloenzyme-mediated disease or disorder is a plant fungal disease or disorder.

6. The method according to claim 5, wherein the plant fungal disease or disorder is caused by a plant fungal pathogen belonging to at least one genera selected from the group consisting of *Blumeria, Podosphaera, Sphaerotheca, Uncinula, Erysiphe, Puccinia, Phakopsora, Gymnosporangium, Hemileia, Uromyces, Alternaria, Cercospora, Cladosporium, Cochliobolus, Colletotrichum, Magnaporthe, Mycosphaerella, Phaeosphaeria, Pyrenophora, Ramularia, Rhyncosporium, Septoria, Venturia, Ustilago, Aspergillus, Penicillium, Drechslera, Fusarium, Botrytis, Gibberella, Rhizoctonia, Pseudocercosporella, Sclerotinia, Helminthosporium, Stagonospora, Exserohilum*, and *Pyricularia*.

7. The method according to claim 5, wherein the plant fungal disease is selected from the group consisting of apple scab, speckled leaf blotch of wheat, leaf spot of sugarbeets, leaf spot of peanut, cucumber anthracnose, wheat leaf rust, grape powdery mildew, wheat powdery mildew, and black sigatoka.

8. The method according to claim 5, wherein the plant fungal disease or disorder is caused by *Venturia inaequalis, Septoria tritici, Cercospora beticola, Cercospora arachidicola, Colletotrichum lagenarium, Puccinia graminis* f. sp. *tritici, Uncinula necator, Blumeria graminis*, or *Mycosphaerella fijiensis*.

9. A process for synthesizing the compound of claim 1, the process comprising contacting a compound of Formula 1:

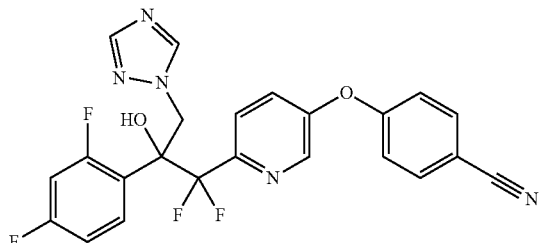

with sulfur in the presence of a suitable solvent to provide the compound of claim 1:

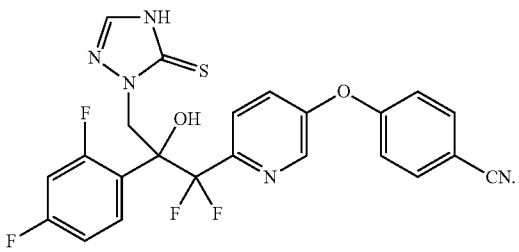 [SMILES: N#Cc1ccc(Oc2ccc(C(F)(F)C(O)(Cn3nc[nH]c3=S)c3ccc(F)cc3F)nc2)cc1]

10. A process according to claim 9, wherein the solvent is N-methyl-2-pyrrolidinone.

11. A process according to claim 9, wherein the reaction is carried out at a temperature within the range of 50 to 200° C.

12. A process according to claim 9, wherein the reaction is carried out in an inert atmosphere.

13. The process according to claim 9, further comprising reacting a compound of Formula D:

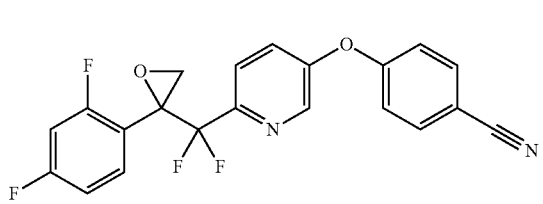

with 1H-1,2,4-triazole in the presence of potassium carbonate and dimethylsulfoxide, wherein the reaction is carried out at a temperature within a range of 15 to 60° C. in an inert atmosphere, to provide the compound of Formula 1:

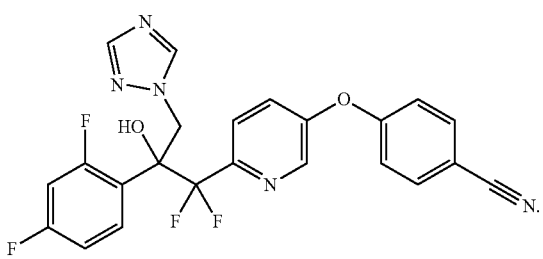

* * * * *